US011957255B2

(12) United States Patent
Lee et al.

(10) Patent No.: US 11,957,255 B2
(45) Date of Patent: Apr. 16, 2024

(54) SMART BOTTLE AND CONTROL METHOD THEREOF

(71) Applicant: Littleone Inc., Gwangju (KR)

(72) Inventors: Byung Kyu Lee, Seoul (KR); Byung Hee Yun, Seoul (KR)

(73) Assignee: LITTLEONE INC., Gwangju (KR)

(*) Notice: Subject to any disclaimer, the term of this patent is extended or adjusted under 35 U.S.C. 154(b) by 1132 days.

(21) Appl. No.: 16/228,790

(22) Filed: Dec. 21, 2018

(65) Prior Publication Data

US 2020/0196782 A1 Jun. 25, 2020

(30) Foreign Application Priority Data

Dec. 20, 2018 (KR) .................. 10-2018-0166671

(51) Int. Cl.
*A61J 9/00* (2006.01)
*A47G 19/22* (2006.01)
(Continued)

(52) U.S. Cl.
CPC ..... *A47G 19/2227* (2013.01); *A47G 19/2288* (2013.01); *A47G 23/16* (2013.01); *A61J 9/00* (2013.01); *G16H 20/60* (2018.01); *A47G 19/2266* (2013.01); *A47J 36/2411* (2013.01); *A47J 36/2444* (2013.01); *A47J 41/0038* (2013.01); *A61J 2200/42* (2013.01); *A61J 2200/72* (2013.01); *F25D 2331/803* (2013.01); *H05B 1/0244* (2013.01)

(58) Field of Classification Search
CPC ............ A47G 19/2227; A47G 19/2288; A47G 19/2266; A47G 23/16; A47J 36/2411;
(Continued)

(56) References Cited

U.S. PATENT DOCUMENTS 2,655,279 A * 10/1953 Wolf ...................... A61J 9/006
215/11.1
2,744,529 A * 5/1956 Tichy ....................... A61J 9/00
215/11.4
(Continued)

FOREIGN PATENT DOCUMENTS

KR 1020170057026 5/2017
KR 10-2018-0035662 A 4/2018
(Continued)

*Primary Examiner* — Gideon R Weinerth
(74) *Attorney, Agent, or Firm* — INVENSTONE PATENT, LLC

(57) ABSTRACT

Provided are a smart bottle and a method for controlling the smart bottle. A smart bottle comprises a bottle for containing liquid; a base formed to be combined to one side of the bottle; a first sensor installed in the bottle or the base, and configured to obtain level information of liquid contained in the bottle; a third sensor configured to obtain inclination information of the bottle; a heater configured to heat the liquid contained in the bottle; a controller configured to control operation of the heater based on the temperature information, determine a feeding start and a feeding end based on the inclination information, and modify the level information based on the inclination information; a communication unit configured to transmit the inclination information and the level information to an external device; and a battery configured to supply power to the first sensor and the base.

15 Claims, 9 Drawing Sheets

(51) Int. Cl.
*A47G 23/16* (2006.01)
*A47J 36/24* (2006.01)
*G08B 21/18* (2006.01)
*G16H 20/60* (2018.01)
*A47J 41/00* (2006.01)
*H05B 1/02* (2006.01)

(58) Field of Classification Search
CPC ...... A47J 36/2444; A47J 41/0038; A61J 9/00;
A61J 2200/42; A61J 2200/72; A61J
2200/70; F25D 2331/803; G16H 20/60;
H05B 1/0244; A61B 2562/0219
USPC ......... 219/438; 215/11.1–11.5, 388; 600/595
See application file for complete search history.

(56) References Cited

U.S. PATENT DOCUMENTS

| | | | | |
|---|---|---|---|---|
| 2,868,203 A * | 1/1959 | Tichy | A61J 9/00 | 215/11.4 |
| 3,044,650 A * | 7/1962 | Oltion | A61J 11/002 | 215/11.1 |
| 3,247,360 A * | 4/1966 | Ponder | A47J 36/2433 | 215/11.4 |
| 3,346,133 A * | 10/1967 | Herdman | A61J 9/00 | 215/11.1 |
| 3,547,296 A * | 12/1970 | Greenberg | A61J 11/0005 | 215/11.4 |
| 3,704,803 A * | 12/1972 | Ponder | A61J 9/006 | 215/11.4 |
| 4,165,641 A * | 8/1979 | Pomerantz | G01F 23/26 | 73/304 C |
| 4,972,391 A * | 11/1990 | Juve | G04G 15/006 | 368/100 |
| 5,208,896 A * | 5/1993 | Katayev | H05B 1/0269 | 219/521 |
| 5,873,474 A * | 2/1999 | Gray | A61J 9/006 | 215/11.4 |
| 6,411,777 B2 * | 6/2002 | Roberson | A47J 31/56 | 392/444 |
| 6,886,139 B2 * | 4/2005 | Liu | G06Q 10/109 | 715/963 |
| 6,951,166 B1 * | 10/2005 | Sickels | A47J 31/401 | 366/144 |
| 7,600,423 B1 * | 10/2009 | Fluhler | G01F 23/26 | 73/304 R |
| 8,759,722 B2 * | 6/2014 | Bolbanat | A47J 36/2438 | 219/432 |
| 9,035,222 B2 * | 5/2015 | Alexander | A47J 39/025 | 165/61 |
| 9,138,097 B2 * | 9/2015 | Driel | A47J 36/2433 | |
| 9,480,363 B2 * | 11/2016 | Delattre | A47J 36/2433 | |
| 9,629,783 B2 * | 4/2017 | Kim | A61J 9/0646 | |
| 9,782,036 B2 * | 10/2017 | Alexander | A47J 36/2433 | |
| 9,802,739 B2 * | 10/2017 | Oldani | B65D 81/18 | |
| 9,863,695 B2 * | 1/2018 | Alexander | F25D 31/005 | |
| 10,010,213 B2 * | 7/2018 | Alexander | A47J 36/321 | |
| 10,107,547 B1 * | 10/2018 | Kraminer | F25D 31/007 | |
| 10,161,779 B2 * | 12/2018 | Lazzi | G01F 23/241 | |
| 10,188,230 B2 * | 1/2019 | Hambrock | A47G 19/2227 | |
| 10,383,476 B2 | 8/2019 | Alexander et al. | | |
| 10,433,672 B2 * | 10/2019 | Alexander | A47J 36/2433 | |
| 10,434,035 B2 * | 10/2019 | Pineda | A61J 15/0076 | |
| 10,524,987 B1 * | 1/2020 | Almarzooqi | A61J 9/008 | |
| 10,617,805 B2 * | 4/2020 | Gaskin | A61J 9/00 | |
| 10,682,285 B2 * | 6/2020 | Levin | G09B 5/04 | |
| 10,729,620 B2 * | 8/2020 | Goodin | A47J 43/046 | |
| 10,750,842 B2 * | 8/2020 | Sengupta | A61B 5/02438 | |
| 10,874,592 B2 * | 12/2020 | Pyka | A61J 9/063 | |
| 10,959,569 B2 * | 3/2021 | Duineveld | A47J 36/2438 | |
| 11,166,575 B2 * | 11/2021 | Richard | A47G 19/2266 | |
| 11,311,129 B1 * | 4/2022 | Chen | A47G 19/2227 | |
| 11,596,263 B1 * | 3/2023 | Siann | A61L 2/07 | |
| 11,744,779 B1 * | 9/2023 | McGrattan | A61B 5/7246 | 600/590 |
| 2004/0060888 A1 * | 4/2004 | Ahn | F16K 15/08 | 215/11.1 |
| 2005/0150393 A1 * | 7/2005 | Biderman | A47J 31/40 | 99/330 |
| 2007/0008163 A1 * | 1/2007 | Drake | G08B 21/24 | 340/686.1 |
| 2008/0041859 A1 * | 2/2008 | Teglbjarg | A47J 36/2461 | 220/592.16 |
| 2008/0251063 A1 * | 10/2008 | Palena | F24V 30/00 | 126/263.09 |
| 2009/0109798 A1 * | 4/2009 | West | G09B 23/281 | 368/10 |
| 2011/0029262 A1 * | 2/2011 | Barkhouse | G01F 23/20 | 702/55 |
| 2011/0087078 A1 * | 4/2011 | Zemel | A61B 5/4312 | 600/300 |
| 2012/0187066 A1 * | 7/2012 | Redl | A47J 41/0038 | 215/11.2 |
| 2012/0305515 A1 * | 12/2012 | Wu | A61J 11/045 | 215/11.1 |
| 2013/0208575 A1 * | 8/2013 | Sammut | G04G 13/021 | 368/250 |
| 2014/0190357 A1 * | 7/2014 | Mak | A47J 36/2438 | 99/453 |
| 2014/0242213 A1 * | 8/2014 | McCarty | A23L 33/30 | 222/146.2 |
| 2015/0068720 A1 * | 3/2015 | Lipoma | A47J 36/2411 | 165/201 |
| 2015/0153239 A1 * | 6/2015 | Pantchenko | G01K 1/02 | 374/142 |
| 2015/0173561 A1 * | 6/2015 | Foster | A47J 31/401 | 215/11.1 |
| 2015/0196247 A1 * | 7/2015 | Lau | G01F 1/363 | 600/301 |
| 2015/0245723 A1 * | 9/2015 | Alexander | A47J 39/025 | 219/387 |
| 2015/0335184 A1 * | 11/2015 | Balachandran | A47G 19/2227 | 29/428 |
| 2016/0025545 A1 * | 1/2016 | Saltzgiver | G01F 23/26 | 73/304 C |
| 2016/0106258 A1 * | 4/2016 | Yen | A47J 36/32 | 99/281 |
| 2016/0157670 A1 * | 6/2016 | Niron | A47J 31/60 | 426/416 |
| 2017/0087524 A1 * | 3/2017 | Deshpande | B65D 51/2892 | |
| 2018/0140510 A1 * | 5/2018 | Maldonado | A61J 1/1406 | |
| 2018/0197629 A1 * | 7/2018 | Zhou | G16H 20/60 | |
| 2019/0015299 A1 * | 1/2019 | Pyka | A61J 9/06 | |
| 2019/0021548 A1 * | 1/2019 | Eisner | A47J 43/042 | |
| 2019/0096224 A1 * | 3/2019 | Shoham | A61J 9/02 | |
| 2019/0125630 A1 * | 5/2019 | Van Kollenburg | A61J 9/02 | |
| 2019/0298615 A1 * | 10/2019 | Wood | G01N 11/02 | |
| 2019/0318607 A1 * | 10/2019 | Johnson | A61J 1/18 | |
| 2020/0129380 A1 * | 4/2020 | Sazonov | A61J 9/008 | |
| 2020/0196782 A1 * | 6/2020 | Lee | A61J 11/008 | |
| 2020/0297137 A1 * | 9/2020 | Richard | A61J 9/006 | |
| 2021/0321803 A1 * | 10/2021 | Zimbelman | A47G 23/16 | |
| 2021/0350920 A1 * | 11/2021 | Vleugels | G16H 50/70 | |
| 2021/0369184 A1 * | 12/2021 | Tiemann | G16H 20/60 | |
| 2021/0386370 A1 * | 12/2021 | Van Der Zwan | A61B 5/74 | |
| 2022/0400978 A1 * | 12/2022 | Tiemann | A61J 9/00 | |
| 2022/0401033 A1 * | 12/2022 | Tiemann | A61J 9/00 | |
| 2023/0085563 A1 * | 3/2023 | Detmer | G09B 19/0092 | |
| 2023/0144707 A1 * | 5/2023 | Lee | A61L 2/24 | 215/11.6 |
| 2023/0201079 A1 * | 6/2023 | Sazonov | A61J 9/001 | 215/11.5 |

FOREIGN PATENT DOCUMENTS

KR 10-2018-0129619 A 12/2018
WO WO 2018/122173 * 7/2018 ................ A61J 9/00

* cited by examiner

SMART BOTTLE AND CONTROL METHOD THEREOF

CROSS-REFERENCE TO RELATED APPLICATIONS

This application claims priority to Korean Patent Application No. 10-2018-0166671 filed on Dec. 20, 2018 in Korea, the entire contents of which are hereby incorporated by reference in their entirety.

BACKGROUND OF THE INVENTION

Field of the Invention

The present invention relates to a smart bottle and, more particularly, to a smart bottle capable of measuring the amount of feeding and a feeding pattern and a method for controlling the smart bottle.

Related Art

A bottle is a container used to contain liquid. Among them, feeding bottles are generally used for lactation. However, the amount of feeding and the number of feedings recommended for babies depend on such factors as the number of months and weight of the baby; and a suitable formula preparation temperature also depends on the type of formula. Therefore, for the case of baby-care, a caregiver usually remembers the formula preparation and records the amount per feeding and the number of feedings by handwriting. Along with recent advances of the Internet of Things (IoT) technology, there is growing demand for more convenient formula preparation and feeding methods in the field of baby-care.

Related to the above, the Korean patent laid-open publication No. 10-2017-0057026 (Publication date: May 24, 2017) "The nursing bottle warmer and the method of nursing management" discloses a method for calculating the amount of feeding for a baby by measuring the weight of a nursing bottle and managing feeding records of the baby by calculating feeding start and end time. However, in order to measure the amount of feeding and manage feeding records by using the method, the nursing bottle has to be put in a nursing bottle warmer. Therefore, it is not possible to measure the amount of feeding or manage feeding records in such places where the nursing bottle warmer is not prepared. Also, if the nursing bottle warmer is not used on a level surface, weight of the nursing bottle is not accurately measured, which makes it difficult to calculate the amount of feeding accurately.

SUMMARY OF THE INVENTION

An object of the present invention is to provide a smart bottle capable of measuring the amount of feeding and managing feeding records anywhere and anytime; and a method for controlling the bottle.

Another object of the present invention is to provide a smart bottle capable of measuring the amount of feeding accurately and managing feeding records; and a method for controlling the bottle.

Yet another object of the present invention is to provide a smart bottle capable of preparing formula and feeding the formula at an optimal temperature; and a method for controlling the bottle.

According to one aspect of the present invention, a smart bottle comprises a bottle for containing liquid; a base formed to be combined to one side of the bottle; a first sensor installed in the bottle or the base, and configured to obtain level information of the liquid contained in the bottle, wherein the base comprises a second sensor configured to obtain temperature information of the bottle; a third sensor configured to obtain inclination information of the bottle; a heater configured to heat the liquid contained in the bottle; a controller configured to control operation of the heater based on the temperature information, determine a feeding start and a feeding end based on the inclination information, and modify the level information based on the inclination information; a communication unit configured to transmit the inclination information and the level information modified by the controller to an external device; and a battery configured to supply power to the first sensor and the base.

According to one perspective of the present invention, the third sensor includes at least one of a gyro sensor and an acceleration sensor; and the controller may calculate the inclination information from angular velocity information measured by the gyro sensor or the inclination information from acceleration information measured by the acceleration sensor.

According to another perspective of the present invention, if the inclination angle of the bottle is larger than a preconfigured angle for more than a preconfigured period, the controller determines that feeding has been started and if the inclination angle of the bottle is less than the preconfigured angle after preconfigured duration, determines that feeding has been ended.

According to yet another perspective of the present invention, if it is determined that the inclination angle of the bottle deviates from the preconfigured angle within the preconfigured period, the controller may control the heater so that internal temperature of the bottle is kept to a preconfigured temperature.

According to still another perspective of the present invention, the controller, based on inclination information measured by the third sensor before the time at which it is determined that the feeding has been started, may generate first level information by modifying level information measured by the at least one first sensor at the corresponding time; based on inclination information measured by the third sensor after the time at which it is determined that the feeding has been ended, generate second level information by modifying level information measured by the at least one sensor at the corresponding time; and determine a difference between the first level information and the second level information as the amount of feeding at the corresponding cycle.

According to a further perspective of the present invention, the first sensor may be composed of a plurality of resistive sensors, the plurality of resistive sensors may be installed along the periphery of the bottle at preconfigured intervals from a lower side of the bottle to an upper side thereof, and the controller may modify level information obtained from voltage values measured by the plurality of resistive sensors by using the inclination information.

According to an additional perspective of the present invention, the first sensor may be composed of at least one capacitance level sensor, wherein the at least one capacitance level sensor is installed on one side surface of the bottle, and the controller may modify level information obtained from a capacitance value measured by the at least one capacitance level sensor by using the inclination information.

According to yet another additional perspective of the present invention, the first sensor may be composed of a plurality of weight sensors, wherein the plurality of weight sensors are installed in the base at preconfigured intervals, and the controller may modify the error of weight information measured by the plurality of weight sensors based on the inclination information.

According to still another additional perspective of the present invention, the controller may operate in a formula preparation mode in which the heater is controlled to operate until it reaches a formula preparation temperature and in a feeding mode in which the heater is controlled to maintain a feeding temperature; and if a measurement value of the third sensor is above a threshold value in the formula preparation mode, control the base to switch to the feeding mode.

According to a further additional perspective of the present invention, when the temperature information reaches the formula preparation temperature for the first time in the formula preparation mode, the controller may control the base to generate an alarm and when the formula preparation temperature is reached again after the bottle leaves the formula preparation temperature, control the base not to generate an alarm within a grace period.

According to a still further additional perspective of the present invention, the base further comprises a motor configured to generate vibrations, and when it is determined that an inclination angle of the bottle is above a preconfigured angle for more than a preconfigured period, and the temperature information is above a preconfigured temperature, the controller may drive the motor.

According to a yet still further additional perspective of the present invention, the second sensor and the heater may be located in an upper part of the base, and in a lower part of the bottle, a recess to receive the second sensor may be formed.

According to another aspect of the present invention, a method for operating a device formed to be combined to one side of a bottle may comprise controlling operation of a heater included in the device based on temperature information of the bottle; when the temperature information reaches a preconfigured temperature, determining a feeding start and a feeding end based on inclination information obtained from a sensor included in the sensor; modifying level information measured at the feeding start time and the feeding end time based on the inclination information; and transmitting, to an external device, at least one of the inclination information, modified feeding information, and information about the amount of feeding calculated based on the modified level information.

According to yet another aspect of the present invention, a method for operating a portable terminal communicating with a device formed to be combined to one side of a bottle configured to contain liquid may comprises receiving inclination information of the bottle from the device; determining a feeding start and a feeding end based on the inclination information; based on inclination information before the feeding start time, generating first level information by modifying level information at the corresponding time; based on inclination information after the feeding end time, generating second level information by modifying level information at the corresponding time; determining a difference between the first level information and the second level information as the amount of feeding at the corresponding cycle; and recording information about the feeding start time, information about the feeding end time, and information about the amount of feeding.

DESCRIPTION OF EXEMPLARY EMBODIMENTS

In what follows, embodiments of the present invention will be described in detail with reference to appended drawings so that those skilled in the art to which the present invention belongs may readily apply the present invention. However, the present invention may be implemented in various other forms and is not limited to a specific embodiment described in this document. Moreover, to describe the present invention without ambiguity, those elements not related to the description of the present invention have been omitted, and throughout the document, similar elements are given a similar reference symbol number.

Throughout the document, unless otherwise explicitly stated, if a particular element is said to "include" some particular element, it means that the former may further include other particular elements rather than exclude them.

Figure 1:
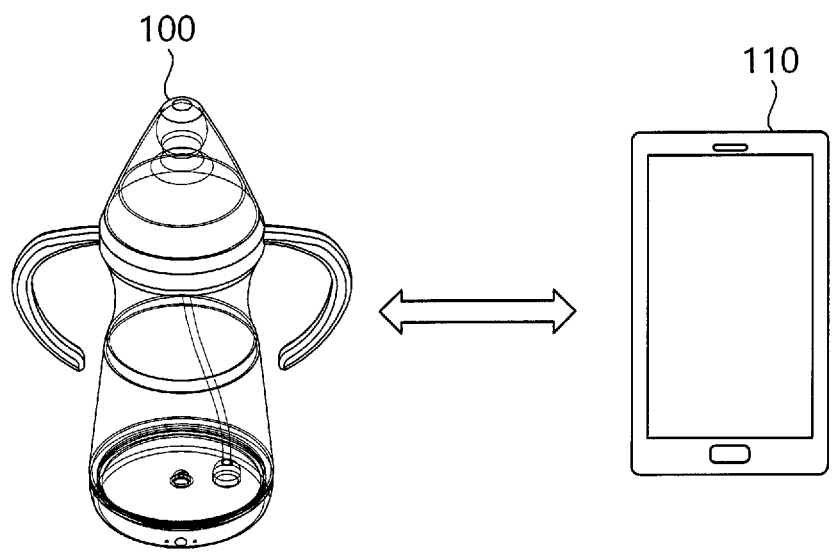
FIG. 1 illustrates a feeding management system according to one embodiment of the present invention.

FIG. 1 illustrates a feeding management system according to one embodiment of the present invention.

Referring to FIG. 1, a feeding management system according to one embodiment of the present invention may comprise a smart bottle 100 and a portable terminal 110.

The smart bottle 100 may transmit feeding-related information such as temperature information, inclination information, level information of the bottle, and information about the amount of feeding to the portable terminal 110 through short-range communication. To this end, the smart bottle 100 may include a base device which may be attached to or detached from the bottle. According to one embodiment as shown in FIG. 1, the base device, being installed in a lower side of the bottle, may communicate with the portable terminal 100 based on the short-range communication standard such as Wireless Fidelity (WiFi) or Bluetooth. Meanwhile, although not shown in the figure, the feeding management system according to one embodiment of the present invention may further comprise a relay device. For example, the relay device, which is intended for relaying communication between the smart bottle 100 and the portable terminal 110, may communicate with the smart bottle 100 based on the Bluetooth and communicate with the portable terminal 110 based on the WiFi.

The portable terminal 110 refers to all kinds of devices which may be carried by a user, including not only smallsized devices such as a tablet, smartphone, or smart watch but also such devices as a laptop computer or notebook computer.

An application for exchanging information with the smart bottle 100 may be installed in the portable terminal 110. The application may obtain feeding-related information from the smart bottle 100 by using the portable terminal 110 and record the obtained information in a memory installed in the portable terminal 110. And based on the information about the number of months from birth received from the user through the portable terminal 110 and feeding-related information received from the smart bottle 100, the application may generate feeding pattern information about the corresponding baby and display the feeding-related information recorded in the portable terminal 110 and the feeding pattern information through the display of the portable terminal 110.

Also, based on the formula information obtained through the portable terminal 110, the application may obtain recommended temperature information for formula preparation about the corresponding formula and control the portable terminal 110 to transmit the recommended temperature information for formula preparation to the smart bottle 110. In this case, the smart bottle 110 may configure the formula preparation temperature according to recommended temperature information for formula preparation received from the portable terminal 110. The formula information may be obtained from an image captured by a camera of the portable terminal 110, Universal Product Code (UPC), European Article Number 13 (EAN13), barcode, or Quick Response (QR) code; or received from the user through the portable terminal 110.

Meanwhile, based on the information about the number of months from birth received from the user through the portable terminal 110 and feeding-related information received from the smart bottle 100, the application may generate feeding pattern information about the corresponding baby as shown in Table 1.

TABLE 1

| Months | Number of feedings (in 24 hours) | Term | Duration |
|---|---|---|---|
| <1 | 10~12 | 1:30~2:00 | 0:10~0:40 |
| 1~2 | 10 | 2:00~2:30 | 0:10~0:30 |
| 3~4 | 8 | 2:30~3:00 | 0:10~0:30 |
| 5~6 | 6~7 | 3:00 | 0:10~0:30 |
| ≥7 | 6 | 3:30 | 0:10~0:30 |

Based on the feeding pattern information as shown in Table 1, when it approaches the next feeding schedule, the application may provide an alarm to notify the user of feeding preparation by using the portable terminal 110. For example, if it is determined, from the feeding-related information received from the smart bottle 100, that feeding has ended at 12:00 while a baby is 7 months old, the application may determine, based on the information about the term for babies older than 7 months, that the next feeding schedule is at 03:30 and provide an alarm for the user to notify of feeding preparation through a push, vibration, or sound function of the portable terminal 110 at 03:20, ten minutes before the next feeding schedule.

Also, the application may compare the feeding pattern information of the corresponding baby with that of babies corresponding to the same number of months from birth on the basis of regions, ages and/or sexes.

Besides, the application may provide the user with a function for configuring a formula preparation temperature and feeding temperature, a function for selecting between the formula preparation mode and the feeding mode, and so on.

In what follows, with reference to FIGS. 2 and 3, a smart bottle according to one embodiment of the present invention will be described in more detail.

Figure 2:
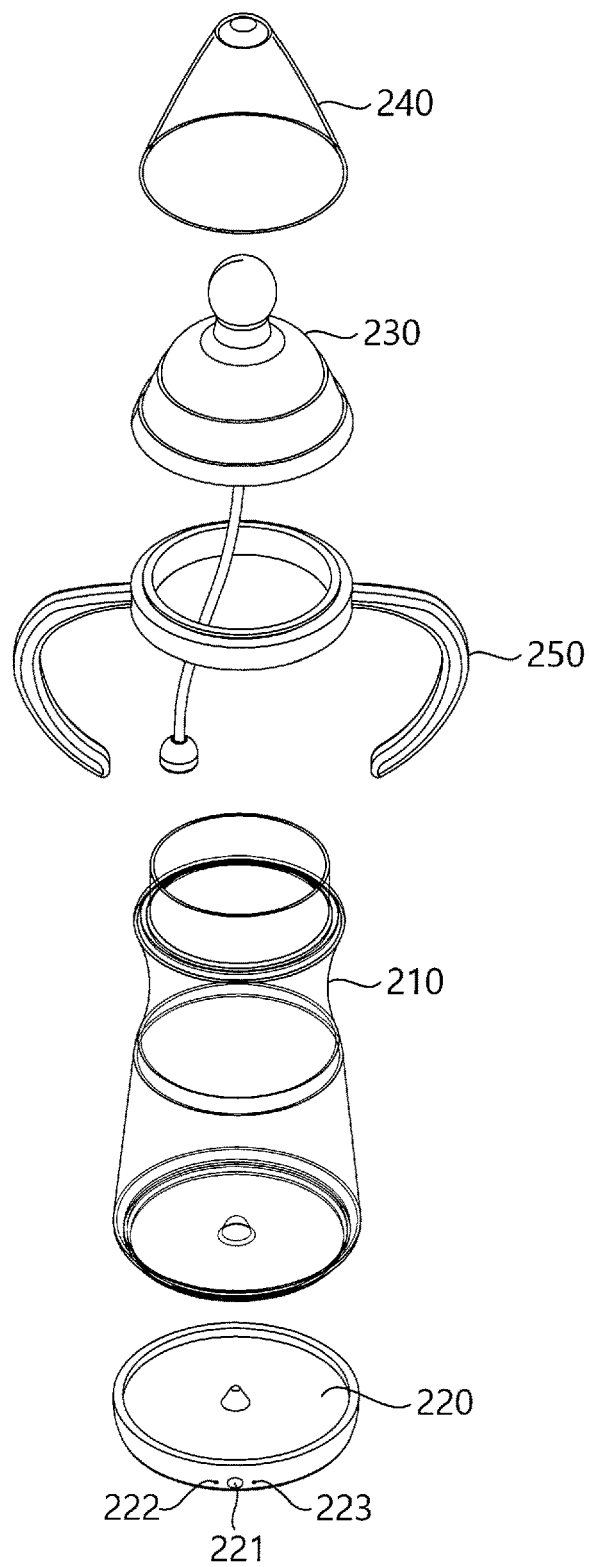
FIG. 2 illustrates a smart bottle according to one embodiment of the present invention.
Figure 3:
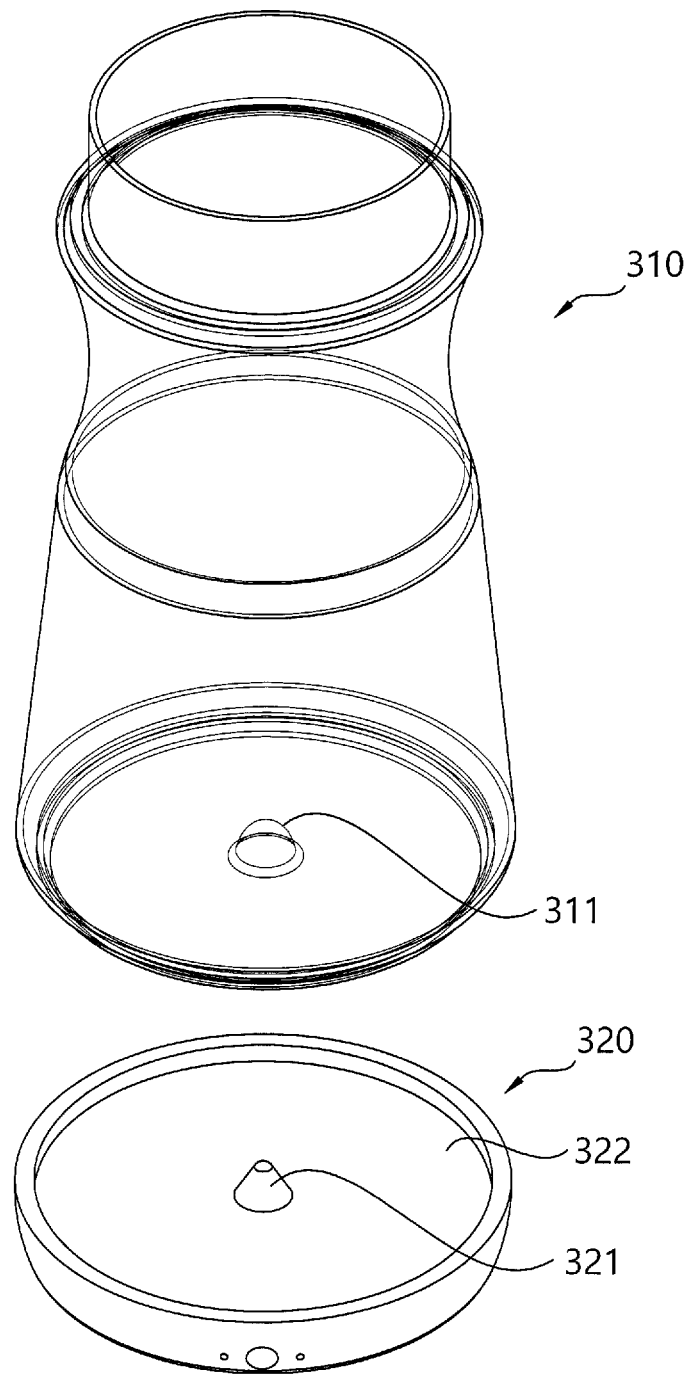
FIG. 3 illustrates a structure of a smart bottle according to one embodiment of the present invention.

FIG. 2 illustrates a smart bottle according to one embodiment of the present invention, and FIG. 3 illustrates a structure of a smart bottle according to one embodiment of the present invention.

First, referring to FIG. 2, a smart bottle may include a bottle 210, base 220, teat 230, bottle cover 240, and handle 250.

The bottle 210 is so formed to contain water, formula, or milk. The bottle 210 may be made by various materials such as glass or plastic depending on the needs. Although not shown in FIG. 2, the bottle 210 may be equipped with a level sensor for measuring the level of liquid inside the bottle. For example, the level sensor may be implemented by a plurality of resistive sensors or at least one capacitance level sensor. A method for measuring a level by using the sensor will be described later.

The base 220 may be formed so as to be combined to one side of the bottle 210. The base 220 may include at least one button 221 and at least one indicator lamp 222, 223. As one example, FIG. 2 illustrates a case in which the base 220 includes one button 221 and two indicator lamps 222, 223. The button 221 may be used to turn on/off power of the base 220 or switch between the formula preparation mode and the feeding mode. The first indicator lamp may indicate information about feeding. And the second indicator lamp 223 may indicate information about formula preparation. As one example, the first indicator lamp 222 may turn red when the temperature is inappropriate for feeding but turn green when appropriate. The second indicator lamp 223 may turn red when the temperature is inappropriate for formula preparation but turn green when appropriate. When a problem occurs in the base 220 (for example, operation failure or low battery), the first 222 and the second indicator lamp 223 may flash to notify the user of the occurrence of the problem.

The teat 230 may be implemented in a replaceable form depending on the number of months from birth and feeding rate of a baby. As shown in FIG. 2, at one side of the teat 230, a straw may be combined. In this case, a weight may be attached to the straw to prevent the baby from suffering abdominal pain. The straw may be made of a material with predetermined elasticity so that the straw may be positioned in the liquid within the bottle 210 by the weight even if the bottle 210 is inclined.

The bottle cover 240 may be implemented in a form to cover the teat to prevent the teat from being contaminated.

The handle 250 may be implemented in a form to be attached to or detached from the bottle 210 depending on the needs.

Meanwhile, referring to FIG. 3, in an upper side of the base 320, a temperature sensor 321 for measuring an internal temperature of the bottle 310 and a heater 322 for heating the liquid within the bottle 310 may be installed. The temperature sensor 321 may be positioned on a protruding part formed on the upper side of the base 320 so that the temperature sensor is separated from the heater 322 by a predetermined distance. If the temperature sensor 321 is not separated from the heater 322 by a predetermined distance, the temperature sensor 321 may not be able to measure the temperature of the bottle 310 accurately due to the heat generated by the heater 322. Therefore, it is preferable that the temperature sensor 321 is installed on the protruding part of the upper side of the base 320, and to this purpose, a recess 311 may be formed in a lower side of the bottle 310 to contain the temperature sensor 321.

In what follows, with reference to FIG. 4, a structure of the base 320 will be described in more detail.

Figure 4:
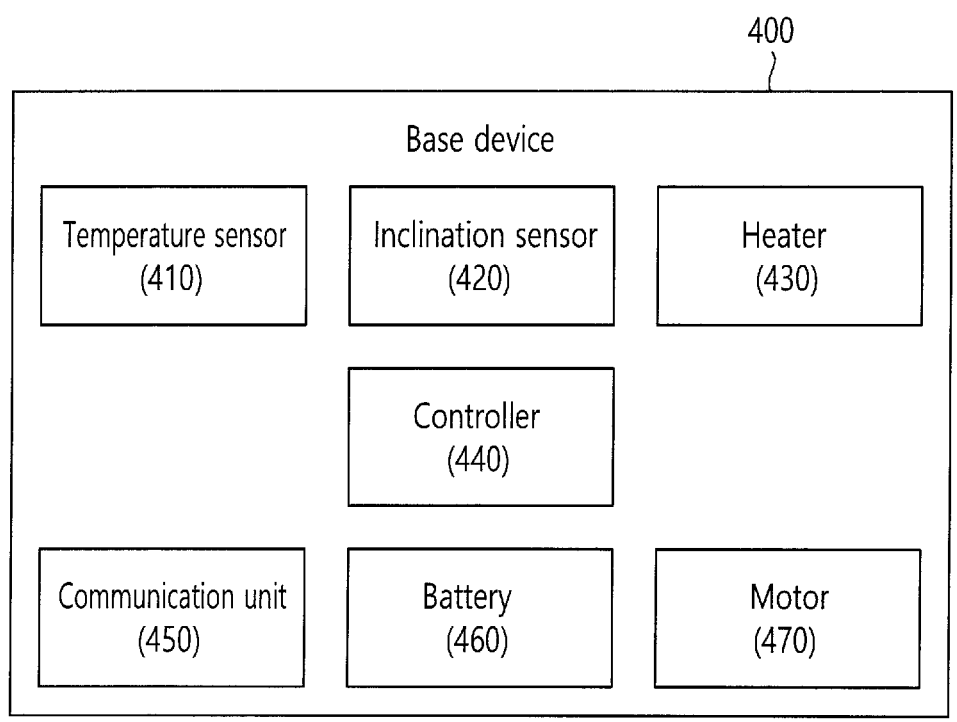
FIG. 4 illustrates an internal structure of a base according to one embodiment of the present invention.

FIG. 4 illustrates an internal structure of a base according to one embodiment of the present invention.

Referring to FIG. 4, a base device 400 may comprise a temperature sensor 410, inclination sensor 420, heater 430, controller 440, communication unit 450, battery 460, and motor 470.

The temperature sensor 410 may be constructed so as to obtain temperature information of a bottle. To this end, as described above, the temperature sensor 410 may be implemented in a protruding form on one side of the base device 400 so as to be separated from the heater 430 by a predetermined distance.

The inclination sensor 420 may be constructed so as to obtain inclination information of the bottle. As one example, the inclination sensor 420 may be implemented by using either a gyro sensor or an acceleration sensor. When a gyro sensor is used as the inclination sensor 420, inclination information may be calculated from angular velocity information measured by the gyro sensor. When an acceleration sensor is used as the inclination sensor 420, inclination information may be calculated from acceleration information measured by the acceleration sensor. The inclination information may be transmitted periodically to a portable terminal.

The heater 430 may be constructed to heat the liquid contained in the bottle. To this end, the heater 430 may be installed in the form of a plate in an upper side of the base device 400 as described above.

The controller 440 may perform a process processed in the base device 400. For example, the controller 440 may control operation of the heater 430 based on the temperature information measured by the temperature sensor 410. The controller 440 may control the temperature information measured by the temperature sensor 410 to be transmitted periodically to the portable terminal. Also, if a rising rate of the temperature information measured by the temperature sensor 410 is faster than a preconfigured rate, the controller 440 determines that there is no liquid in the bottle, stops operation of the heater 430, and informs of the current situation by using an indicator lamp and/or a motor 470. At this time, the portable terminal may also inform of shortage of liquid through a push, vibration, or sound function.

According to the present invention, the controller 440 may operate in a formula preparation mode and a feeding mode.

The formula preparation mode may be defined as a mode in which the heater 430 is controlled to operate until the formula preparation temperature is reached, and the feeding mode may be defined as a mode in which the heater 430 is controlled to maintain a feeding temperature. Here, the formula preparation temperature denotes a temperature appropriate for making milk by using formula, and the feeding temperature denotes a temperature appropriate for providing milk to a baby. The formula preparation temperature is different according to the type of formula, manufacturer, and so on, which generally is higher than the feeding temperature. As one example, when the base device 400 operates for the first time, the formula preparation temperature may be configured as 40 degrees, and the feeding temperature may be configured as 37 degrees. However, when recommended formula preparation temperature information is received from a portable terminal, the controller 440 may reconfigure the formula preparation temperature according to the received information. The recommended formula preparation temperature information may be obtained from formula information recognized from an image captured by a camera of the portable terminal, UPC, EAN13, barcode, or QR code.

When the formula preparation temperature is reached due to the operation of the heater 430 for the first time in the formula preparation mode, the controller 440 may indicate that formula preparation is completed by using an indicator lamp and/or motor 470 installed in the base device 400. At this time, through a push, vibration, or sound function, the portable terminal may also inform the user that formula preparation is completed.

Also, when the temperature of the bottle reaches the formula preparation temperature again in the formula preparation mode after the bottle leaves the formula preparation temperature, the controller may control the base not to generate an alarm within a grace period to avoid causing inconvenience due to repeated notification.

In the feeding mode, when the user pushes a button installed in the base device 440 or enters a mode switch command to the portable terminal after making milk, the formula preparation mode may be changed to the feeding mode. In general, when making milk, the user performs a motion of shaking a bottle so that the formula powder may be fully dissolved in the water. This motion causes a large change in the inclination, acceleration and/or angular velocity of the bottle. Therefore, when it is determined that a value measured by an inclination sensor in the formula preparation mode is larger than a threshold value, the controller 440 may determine that the user is in the middle of formula preparation and control the base to automatically switch to the feeding mode.

Meanwhile, when it is determined that the inclination angle of the bottle is larger than a preconfigured angle for more than a preconfigured period, the controller 440 may determine that feeding has been started. At this time, when the temperature of the bottle is higher than a preconfigured temperature, the controller 440 drives the motor 470 to inform of a risk of burns in the form of vibration. For example, when a temperature higher than 38 degrees is measured more than 10 times in the formula preparation or feeding mode and the inclination of the bottle is maintained at −1.2 g or above along the x or y-axis for more than 5 seconds with respect to the reference (along the 0-gravitational direction), the controller may determine that feeding has been started and control the motor to generate vibrations. Also, when the inclination is less than −0.5 g or above −9 g with respect to the reference in the feeding mode, the controller 440 may drive the motor 470 to coach the user to feed the baby within an appropriate range of the inclination angle though vibrations.

Meanwhile, when the inclination sensor 420 is implemented by a gyro sensor, the controller 440 may calculate inclination information from angular velocity information measured by the gyro sensor. When the inclination sensor 420 is implemented by an acceleration sensor, the controller 440 may calculate inclination information from acceleration information measured by the acceleration sensor. The controller 440 may determine a feeding start and feeding end based on the inclination information obtained from the inclination sensor 420.

More specifically, when it is determined that the inclination angle of the bottle is larger than a preconfigured angle for more than a preconfigured period, the controller 440 may determine that feeding has been started and when it is determined that the inclination angle of the bottle is within the preconfigured angle after preconfigured duration, determine that feeding has been ended. At this time, if it is determined that the inclination angle of the bottle leaves the preconfigured angle within the preconfigured duration, the controller may control the heater 470 so that the internal temperature of the bottle is maintained at a preconfigured temperature.

For example, when the inclination of the bottle is such that the x or y-axis is maintained above −1.2 g for more than 5 seconds with respect to the reference, the controller 440 may determine that a condition for starting feeding records has been satisfied. And if a feeding activity is detected for more than 1 minute after the inclination of the bottle satisfies the condition for starting feeding records, the controller 440 may determine a subsequent time at which the condition for starting feeding records is released as the feeding end time. Also, if feeding activity time (a time period during which the inclination angle is maintained above −1.2 g) is less than 1 minute after entering the feeding mode for the first time (including the case of re-entering the feeding mode with an inclination of 0 g), the controller 440 may determine that the user has stopped feeding temporarily and control the heater 430 so that the feeding temperature is maintained up to two hours before the end of feeding. Since milk may go bad after two hours, the controller 440 may stop operation of the heater 430. In this case, the portable terminal may display a pop-up window which advises to prepare formula again.

Meanwhile, a smart bottle according to the present invention may include at least one level sensor. The at least one level sensor may be installed in the bottle or base device 400. The controller 440 may obtain level information of the liquid contained in the bottle by using the at least one level sensor. When the bottle is equipped with the at least one level sensor, the level sensor may be implemented by a resistive sensor and/or capacitance level sensor. When the base device 440 is equipped with the at least one level sensor, the level sensor may be implemented by a weight sensor.

Based on the level information obtained from the level sensor, the controller 440 may determine the amount of feeding at each feeding cycle. Here, a feeding cycle may refer to an interval between the time at which the condition for starting feeding records is satisfied and the time at which the condition for starting feeding records is released. However, if the bottle is not placed on a level surface, the level information is not measured accurately, and therefore the amount of feeding may not be measured accurately. Therefore, the controller 440 of the base device 400 according to the present invention may modify the level information obtained from a level sensor based on the inclination information obtained from the inclination sensor 420. And the controller 440 may calculate the amount of feeding at the corresponding feeding cycle by using the modified level information.

As one example, based on the inclination information measured by the level sensor 420 before the time at which it is determined that feeding has been started in the feeding mode (for example, the time at which the level information exhibits no further change since the level information is measured), the controller 440 may generate first level information by modifying the level information measured by the level sensor at the corresponding time and based on the inclination information measured by the level sensor 420 after the time at which it is determined that feeding has been ended, generate second level information by modifying the level information measured by the level sensor at the corresponding time. And a difference between the first and the second level information may be determined as the amount of feeding at the corresponding feeding cycle. The process for modifying a level and the process for calculating the amount of feeding by the controller 440 as described above may not be performed in the formula preparation mode to reduce power consumption. The process for modifying a level will be described in more detail with reference to FIGS. 5 to 7.

The communication unit 450 may transmit, to an external device (for example, a relay or a portable terminal), temperature information measured by the temperature sensor 410, inclination information measured by the inclination sensor 420, level information measured by the level sensor, level information modified by the controller 440, feeding-related information such as the amount of feeding calculated by the controller 440, information about the remaining amount of a battery 460, and so on. Also, the communication unit 450 may receive feeding temperature configuration information, formula preparation temperature configuration information, mode change information, and the like from the external device.

The battery 460 may be configured to provide power to the base device 400 and a feeding sensor. The controller 440 may check the remaining amount of the battery 460 and if it is determined that the formula preparation temperature and/or feeding temperature may not be reached when the bottle is heated, inform of shortage of the battery 460 by using an indicator lamp and/or motor 470 instead of operating the heater 430. In this case, too, the portable terminal may inform of shortage of the battery 460 through a push, vibration, or sound function.

Figure 5:
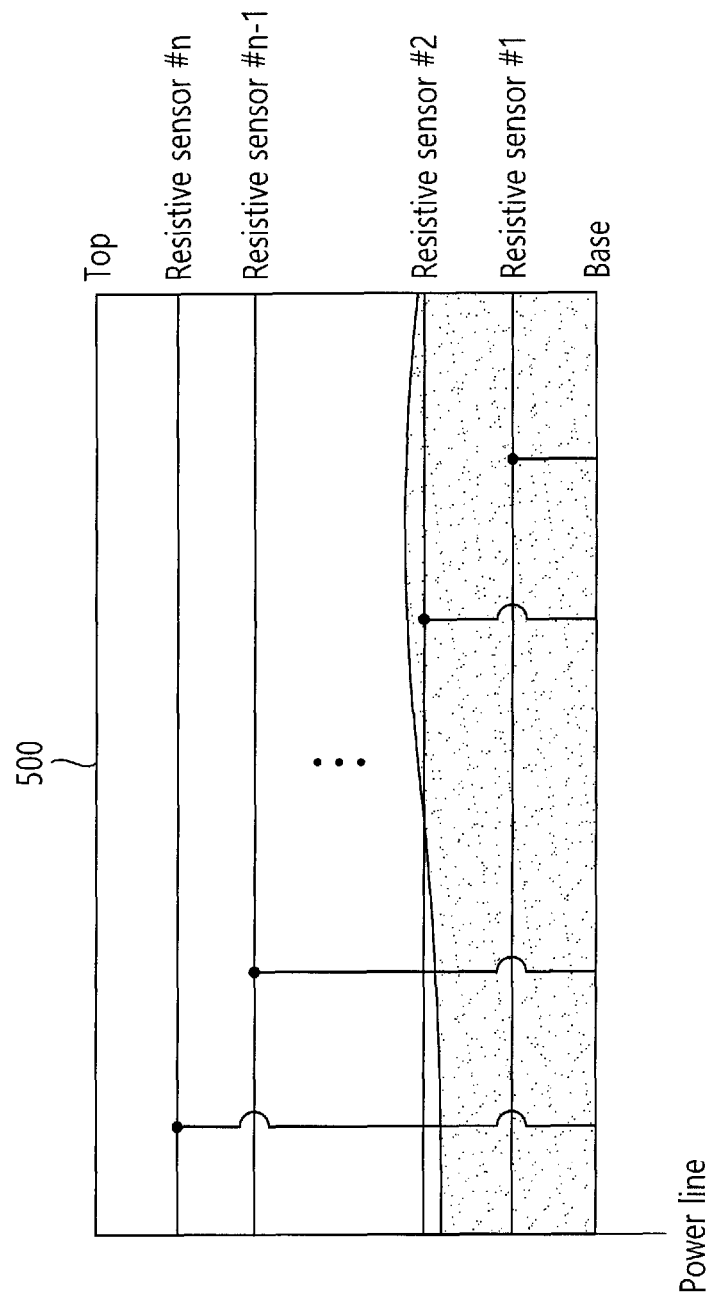
FIG. 5 illustrates a method for measuring a level according to one embodiment of the present invention.

FIG. 5 illustrates a method for measuring a level according to one embodiment of the present invention.

As one example, FIG. 5 illustrates a case where a plurality of resistive sensors (the first resistive sensor to the n-th resistive sensor) are used as a level sensor. The plurality of resistive sensors may be disposed on a sheet 500 and attached along the periphery of the bottle at preconfigured intervals from a lower side of the bottle to an upper side thereof. Here, the sheet 500 may be implemented by a transparent sheet or a translucent sheet and may have a scale indicating the level of liquid for the convenience of the user.

When coming into contact with liquid, a resistive sensor generates a voltage drop due to the resistance of the liquid. Therefore, if position information (or number) of a sensor which has generated a voltage drop and inclination information of the bottle are utilized, level information at the horizontal state may be derived. For example, if a voltage drop is detected at the n-th resistive sensor while the inclination of the bottle is 45 degrees, the controller of the base may determine that the position of the (n/2)-th resistive sensor corresponds to the current level at the horizontal state.

Figure 6:
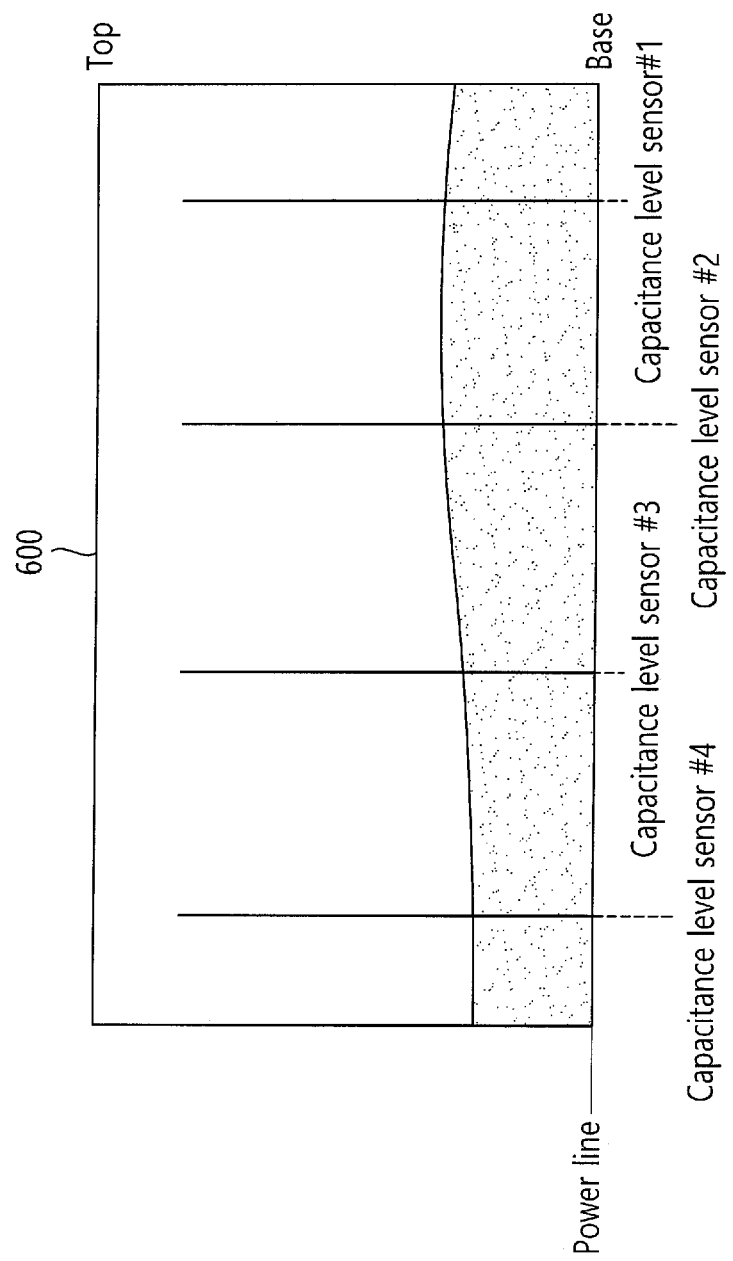
FIG. 6 illustrates a method for measuring a level according to another embodiment of the present invention.

FIG. 6 illustrates a method for measuring a level according to another embodiment of the present invention.

As one example, FIG. 6 illustrates a case where four capacitance level sensors (the first capacitance level sensor to the fourth capacitance level sensor) are used as a level sensor. Each capacitance level sensor may be disposed on a sheet 600 and attached to one side surface of the bottle. One capacitance level sensor is enough for measuring a level, but for more accurate measurement of a level, four capacitance level sensors may be utilized. When four capacitance level sensors are used, they may be disposed at 90 degree angles relative to each other with respect to the center of the bottle. A capacitance level sensor yields its capacitance value in proportion to a level to be measured. Therefore, when a capacitance value measured by each capacitance level sensor, inclination angle of the bottle, and orientation information of the bottle are used, the level information at the horizontal state may be derived. To this end, the controller of the base may map the current capacitance value of a capacitance level sensor, inclination angle of the bottle, and orientation angle of the bottle to a table containing level information at the horizontal state due to a capacitance value, inclination angle of the bottle, and orientation angle of the bottle to derive the level of liquid at the horizontal state.

Figure 7:
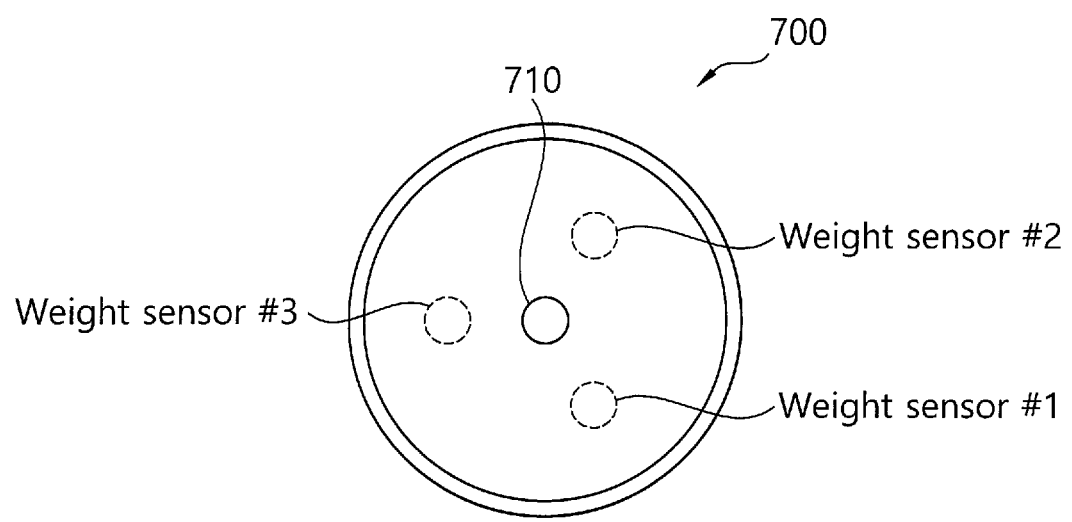
FIG. 7 illustrates a method for measuring a level according to yet another embodiment of the present invention.

FIG. 7 illustrates a method for measuring a level according to yet another embodiment of the present invention.

As one example, FIG. 7 illustrates a case where three weight sensors (the first weight sensor to the third weight sensor) are used as a level sensor. The individual weight sensors may be installed at preconfigured intervals in a base 700 including a protruding part 710.

When only one weight sensor is used for level measurement, a measured weight is different depending on the inclination of the bottle. Therefore, based on the inclination information of the bottle and weight information thereof, the controller of the base may compensate for the error in the weight information measured by each weight sensor and calculate level information at the horizontal state by using the compensated weight information.

Figure 8:
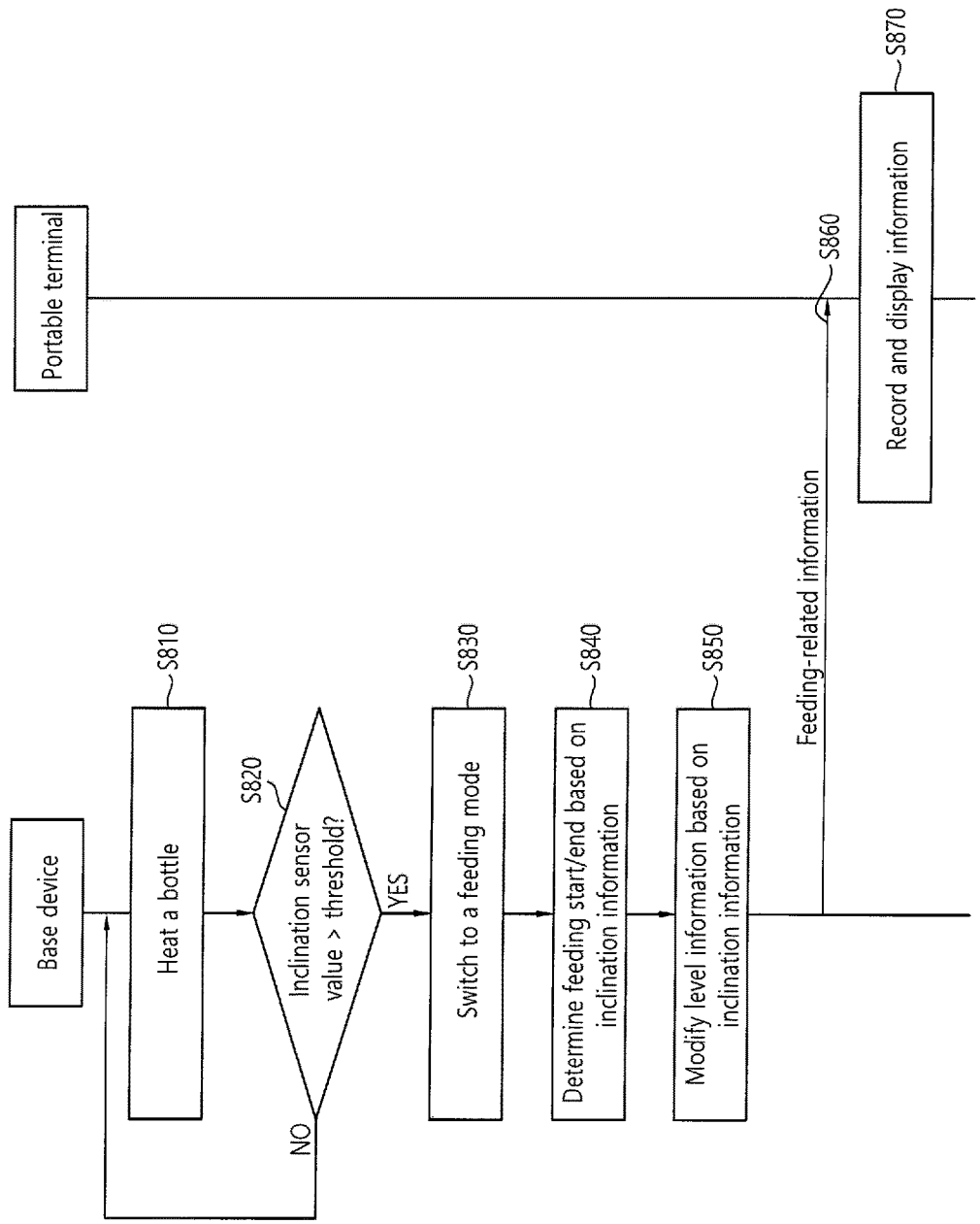
FIG. 8 is a flow diagram illustrating a method for feeding management according to one embodiment of the present invention.

FIG. 8 is a flow diagram illustrating a method for feeding management according to one embodiment of the present invention.

In what follows, with reference to FIG. 8, a method for feeding management by a base device installed in a smart bottle according to the present invention will be described.

A base device may control operation of a heater based on the temperature information of the bottle S810. As one example, the base device may control the heater in the formula preparation mode to reach a formula preparation temperature. And the base device may control the heater in the feeding mode to maintain a feeding temperature. The formula preparation temperature may be set to 40 degrees when the base device is initially operated or configured by the formula preparation temperature configuration information received from a portable terminal. The formula preparation temperature configuration information may be obtained from an image captured through a camera of the portable terminal, barcode, QR code, and so on. The feeding temperature may be set to 37 degrees when the base device is initially operated or configured by the feeding temperature configuration information received from the portable terminal.

The base device may determine whether a value measured by a level sensor in the formula preparation mode exceeds a threshold value S820. If a value measured by the level sensor exceeds the threshold value, the base device may determine that the user is preparing formula and switch to the feeding mode S830.

When temperature information of the bottle reaches a preconfigured temperature, namely when the base device is in the feeding mode, the base device may determine whether feeding has been started or ended based on inclination information S840. As one example, if it is determined that the inclination angle of the bottle is larger than a preconfigured angle (for example, 45 degrees) for more than a preconfigured period (for example, 5 seconds), the base device may determine that feeding has been started. And if it is determined that the inclination angle of the bottle is within the preconfigured angle after a preconfigured period (for example, 1 minute), the base device may determine that feeding has been ended. Also, if it is determined that the inclination angle of the bottle leaves the preconfigured angle within the preconfigured period, the base device may determine that feeding has been stopped temporarily and control the bottle so that the internal temperature of the bottle is maintained at a preconfigured temperature (feeding temperature).

Also, based on the inclination information measured before the time at which it is determined that feeding has been started, the base device may generate first level information by modifying the level information measured at the corresponding time and based on the inclination information measured after the time at which it is determined that feeding has been ended, generate second level information by modifying the level information measured at the corresponding time S850. And the base device may determine a difference between the first and the second level information as the amount of feeding at the corresponding cycle.

Afterwards, the base device may transmit feeding-related information including the inclination information, modified feeding information, and information about the amount of feeding to the portable terminal S860.

If receiving feeding-related information from the base device, the portable terminal records the received feeding-related information and display the corresponding information according to the user's request S870.

Figure 9:
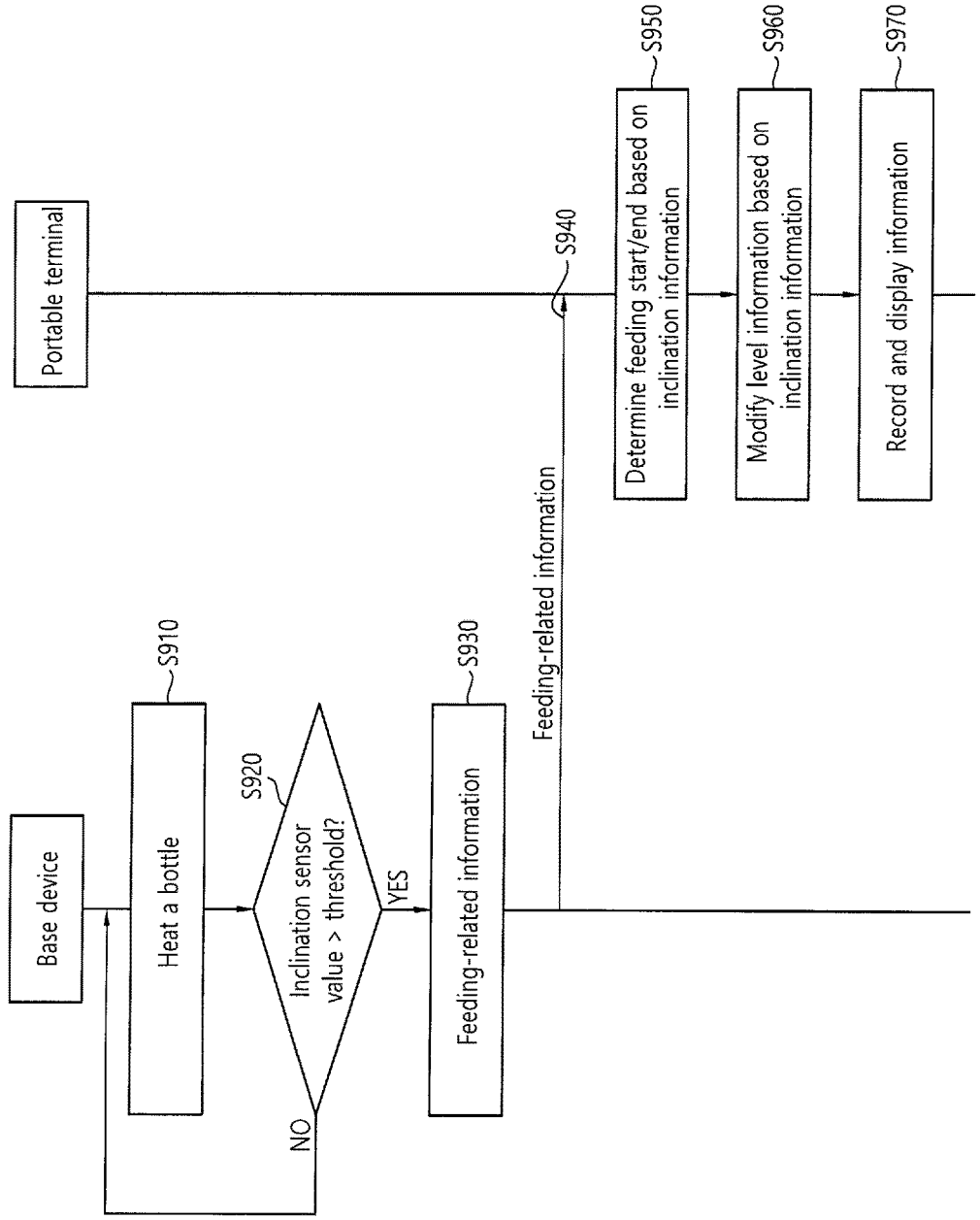
FIG. 9 is a flow diagram illustrating a method for feeding management according to another embodiment of the present invention.

FIG. 9 is a flow diagram illustrating a method for feeding management according to another embodiment of the present invention.

In what follows, with reference to FIG. 9, a method for feeding management by a portable terminal according to the present invention will be described. Since the process illustrated in FIG. 9 (S910 to S930 steps), where a base device heats a bottle in the formula preparation mode and switches the bottle to the feeding mode based on a measurement value from an inclination sensor, is the same as illustrated in FIG. 8, repeated descriptions thereof will be omitted.

In the feeding mode, a base device may transmit feeding-related information to a portable terminal S940. Here, the feeding-related information may include temperature information of a bottle, inclination information of the bottle, and level information.

If feeding-related information is received from the base device, the portable terminal may determine whether feeding has been started or ended based on the inclination information included in the received feeding-related information S950. As one example, if it is determined that the inclination angle of the bottle is larger than a preconfigured angle (for example, 45 degrees) for more than a preconfigured period (for example, 5 seconds), the portable terminal may determine that feeding has been started. At this time, the portable terminal may determine that feeding has been started 3 seconds right before the corresponding time to compensate for a communication delay with the base device. And if it is determined that the inclination angle of the bottle is less than the preconfigured angle after a preconfigured period (for example, 1 minute), the portable terminal may determine that feeding has been ended.

At this time, based on the inclination information measured before the time at which it is determined that feeding has been started, the portable terminal may generate first level information by modifying level information measured at the corresponding time and based on the inclination information measured after the time at which it is determined that feeding has been ended, generate second level information by modifying the level information measured at the corresponding time S960. And the portable terminal may determine a difference between the first and the second level information as the amount of feeding at the corresponding cycle.

Afterwards, the portable terminal may record information about a feeding pattern based on feeding start time information, feeding end time information, information about the amount of feeding, and so on; and display the corresponding information upon the user's request S970.

In one embodiment of the present invention, the portable terminal comprises a communication unit, processor, and memory. The memory, being connected to the processor, stores various kinds of information required to operate the processor. The communication unit, being connected to the processor, transmits and/or receives a radio signal. For example, the communication unit may receive feeding-related information disclosed in the present specification from the base device. Also, the communication unit may transmit, to the base device, formula preparation temperature information, feeding temperature configuration information, mode change information, and so on.

The processor may perform the operation of the portable terminal described with reference to FIG. 9 according to the control of an application. For example, according to one embodiment of the present invention, the processor may determine feeding start and feeding end, modify level information, and calculate the amount of feeding. The memory may store feeding-related information and according to the request of the processor, may provide information corresponding to the processor.

As one example, the processor may include Application-Specific Integrated Circuits (ASICs), other chipsets, logic circuits, and/or data processors. The memory may include Read-Only Memory (ROM), Random Access Memory (RAM), flash memory, memory cards, storage media and/or other storage devices. The communication unit may include a baseband circuit for processing a radio signal. When the above-described embodiment is implemented in software, the above-described scheme may be implemented using a module (process or function) which performs the above function. The module may be stored in the memory and executed by the processor. The memory may be disposed to the processor internally or externally and connected to the processor using a variety of well-known means.

The description given above is intended merely to illustrate technical principles of the present invention, and various changes and modifications may be made by those skilled in the art to which the present invention belongs without deviating from the inherent characteristics of the present invention. Therefore, it should be understood that embodiments disclosed in the present specification are not intended to limit the technical principles of the present invention but to support describing the present invention, and thus the technical scope of the present invention is not limited by the embodiments. The technical scope of the present invention should be judged by the appended claims, and all of the technical principles found within the range equivalent to the technical scope of the present invention should be interpreted to belong thereto.

According to the present invention, since a base for feeding management may be attached to or detached from a bottle, feeding management may be done anytime and anywhere.

Also, since level information measured by a level sensor is modified by using inclination information of a bottle, measurement of the amount of feeding and feeding management may be done accurately.

Moreover, since a heating temperature is adjusted based on a formula preparation mode and a feeding mode, formula preparation and feeding may be done at an optimal temperature.

What is claimed is:

1. An apparatus comprising:
a bottle for containing liquid;
a base formed to be combined to one side of the bottle; and
at least one first sensor installed in the bottle or the base and configured to obtain level information of the liquid contained in the bottle,
wherein the bottle includes a straw suspended inside the bottle, the straw combined with a teat of the bottle,
wherein the straw includes an attached weight configured to position the straw in the liquid contained in the bottle when the bottle is inclined,
wherein the base comprises:
a second sensor configured to obtain temperature information of the bottle;
a third sensor configured to obtain inclination information of the bottle;
a heater configured to heat the liquid contained in the bottle;
a controller configured to
control operation of the heater based on the temperature information,
determine a feeding start and a feeding end based on the inclination information, and
modify the level information based on the inclination information;
a communication unit configured to transmit the inclination information and the level information modified by the controller to a portable terminal; and
a battery configured to supply power to the at least one first sensor and the base,
wherein the controller is further configured to
determine that feeding has started, if the inclination information indicates an inclination angle of the bottle that is greater than a preconfigured angle for more than a preconfigured period,
determine that feeding has ended, if the inclination angle of the bottle is less than the preconfigured angle after a preconfigured duration,
operate the base in a formula preparation mode in which the heater is controlled to operate until an internal temperature of the bottle as indicated by the temperature information reaches a formula preparation temperature, and
control the base in the formula preparation mode in order to not generate a first alarm within a grace period when the formula preparation temperature is reached while the heater operates in the formula preparation mode,
wherein the bottle is a smart bottle configured to transmit feeding-related information to the portable terminal through short-range communication, the feeding-related information including the temperature information, the inclination information, the level information of the bottle, and information about an amount of feeding of a corresponding cycle,
wherein the portable terminal includes an application and is configured to
generate feeding pattern information based on the feeding-related information and the age of a baby expressed as a number of months as input to the portable terminal from a user, compare the feeding pattern information of the baby with that of babies of a same age based on regions, ages, and sexes, and provide a second alarm to notify a next feeding schedule of the baby based on the feeding pattern information, wherein the application of the portable terminal is configured to obtain recommended temperature information for formula preparation, the recommended temperature information based on formula information obtained through the portable terminal, and transmit the recommended temperature information from the portable terminal to the bottle, wherein the bottle configures the formula preparation temperature according to the recommended temperature information received from the portable terminal, and wherein the formula information is obtained from an image captured by a camera of the portable terminal, the captured image including at least one of a Universal Product Code (UPC), a European Article Number 13 (EAN-13), a barcode, and a Quick Response (QR) code.

2. The apparatus of claim 1, wherein the third sensor includes at least one of a gyro sensor and an acceleration sensor; and wherein the controller is further configured to calculate the inclination information from angular velocity information measured by the gyro sensor or calculate the inclination information from acceleration information measured by the acceleration sensor.

3. The apparatus of claim 1, wherein the temperature information indicates an internal temperature of the bottle, and wherein, if it is determined that the inclination angle of the bottle deviates from the preconfigured angle within the preconfigured period, the controller is further configured to control the heater so that the internal temperature of the bottle is kept to a preconfigured temperature.

4. The apparatus of claim 1, wherein the controller is further configured to generate first level information by modifying level information measured at a corresponding time by the at least one first sensor, based on inclination information obtained before a determination by the controller that feeding has started;

generate second level information by modifying level information measured at a corresponding time by the at least one first sensor, based on inclination information obtained after a determination by the controller that feeding has ended; and determine a difference between the first level information and the second level information as the amount of feeding of a corresponding cycle.

5. The apparatus of claim 1, wherein the at least one first sensor is composed of a plurality of resistive sensors, the plurality of resistive sensors are installed along the periphery of the bottle at preconfigured intervals from a lower side of the bottle to an upper side thereof, and the controller is further configured to modify level information obtained from voltage values measured by the plurality of resistive sensors by using the inclination information.

6. The apparatus of claim 1, wherein the at least one first sensor is composed of at least one capacitance level sensor, wherein the at least one capacitance level sensor is installed on one side surface of the bottle, and wherein the controller is further configured to modify level information obtained from a capacitance value measured by the at least one capacitance level sensor by using the inclination information.

7. The apparatus of claim 1, wherein the at least one first sensor is composed of a plurality of weight sensors, wherein the plurality of weight sensors are installed in the base at preconfigured intervals about a centrally disposed part, and wherein the controller is further configured to compensate for an error of weight information measured by each of the plurality of weight sensors based on the inclination information, and calculate level information at a horizontal state by using the compensated weight information.

8. The apparatus of claim 1, wherein the controller is further configured to operate the base in a feeding mode in which the heater is controlled to maintain a feeding temperature; and control the base to switch from the formula preparation mode to the feeding mode, if a measurement value of the third sensor is above a threshold value in the formula preparation mode.

9. The apparatus of claim 8, wherein the base further comprises a motor configured to generate vibrations, and wherein the controller is further configured to drive the motor when it is determined that the inclination angle of the bottle is above a preconfigured angle for more than a preconfigured period and that the temperature information is above a preconfigured temperature.

10. The apparatus of claim 1, wherein the base includes an upper part facing the bottle, the upper part of the base including the second sensor and the heater, wherein the second sensor is disposed on a protruding part formed on the upper part of the base so that the second sensor is separated from the heater by a predetermined distance in an axial direction of the bottle, and wherein the bottle includes a lower part facing the base, the lower part of the bottle including a recess configured to receive the protruding part.

11. The apparatus of claim 1, wherein the straw is made of an elastic material, and wherein the attached weight is disposed at a distal end of the straw.

12. A method for operating a device formed to be combined to one side of a bottle, the method comprising:

controlling operation of a heater included in the device based on temperature information of the bottle;

determining, when the temperature information reaches a preconfigured temperature, a feeding start and a feeding end based on inclination information obtained from a sensor included in the sensor;

modifying level information measured at the feeding start time and the feeding end time based on the inclination information; and transmitting, to a portable terminal, at least one of the inclination information, the modified feeding information, and information about an amount of feeding calculated based on the modified level information, the method further comprising
   determining that feeding has started, if the inclination information indicates an inclination angle of the bottle that is greater than a preconfigured angle for more than a preconfigured period,
   determining that feeding has ended, if the inclination angle of the bottle is less than the preconfigured angle after a preconfigured duration,
   operating the base in a formula preparation mode in which the heater is controlled to operate until an internal temperature of the bottle as indicated by the temperature information reaches a formula preparation temperature, and
   controlling the base in the formula preparation mode in order to not generate a first alarm within a grace period when the formula preparation temperature is reached while the heater operates in the formula preparation mode,
wherein the bottle is a smart bottle configured to transmit feeding-related information to the portable terminal through short-range communication, the feeding-related information including the temperature information, the inclination information, the level information of the bottle, and information about an amount of feeding of a corresponding cycle, and
wherein the portable terminal includes an application and is configured to
   generate feeding pattern information based on the feeding-related information and the age of a baby expressed as a number of months as input to the portable terminal from a user,
   compare the feeding pattern information of the baby with that of babies of a same age based on regions, ages, and sexes, and
   provide a second alarm to notify a next feeding schedule of the baby based on the feeding pattern information,
the method further comprising suspending a straw inside the bottle, the straw combined with a teat of the bottle,
wherein the straw includes an attached weight configured to position the straw in the liquid contained in the bottle when the bottle is inclined,
wherein the application of the portable terminal is configured to
   obtain recommended temperature information for formula preparation, the recommended temperature information based on formula information obtained through the portable terminal, and
   transmit the recommended temperature information from the portable terminal to the bottle,
wherein the bottle configures the formula preparation temperature according to the recommended temperature information received from the portable terminal, and
wherein the formula information is obtained from an image captured by a camera of the portable terminal, the captured image including at least one of a Universal Product Code (UPC), a European Article Number 13 (EAN-13), a barcode, and a Quick Response (QR) code.

13. The method of claim 12,
wherein the straw is made of an elastic material, and
wherein the attached weight is disposed at a distal end of the straw.

14. A method for operating a portable terminal communicating with a device formed to be combined to one side of a bottle configured to contain liquid, the method comprising:
   receiving inclination information of the bottle from the device;
   determining a feeding start and a feeding end based on the inclination information;
   generating, based on inclination information before the feeding start time, first level information by modifying level information at the corresponding time;
   determining, based on inclination information after the feeding end time, second level information by modifying level information at the corresponding time;
   determining a difference between the first level information and the second level information as an amount of feeding at the corresponding cycle; and
   recording information about the feeding start time, information about the feeding end time, and information about the amount of feeding,
the method further comprising
   determining that feeding has started, if the inclination information indicates an inclination angle of the bottle that is greater than a preconfigured angle for more than a preconfigured period, and
   determining that feeding has ended, if the inclination angle of the bottle is less than the preconfigured angle after a preconfigured duration;
   operating the base in a formula preparation mode in which the heater is controlled to operate until an internal temperature of the bottle as indicated by the temperature information reaches a formula preparation temperature, and
   controlling the base in the formula preparation mode in order to not generate a first alarm within a grace period when the formula preparation temperature is reached while the heater operates in the formula preparation mode,
wherein the bottle is a smart bottle configured to transmit feeding-related information to the portable terminal through short-range communication, the feeding-related information including the temperature information, the inclination information, the level information of the bottle, and information about an amount of feeding of a corresponding cycle, and
wherein the portable terminal includes an application and is configured to
   generate feeding pattern information based on the feeding-related information and the age of a baby expressed as a number of months as input to the portable terminal from a user,
   compare the feeding pattern information of the baby with that of babies of a same age based on regions, ages, and sexes, and
   provide a second alarm to notify a next feeding schedule of the baby based on the feeding pattern information,
the method further comprising suspending a straw inside the bottle, the straw combined with a teat of the bottle,
wherein the straw includes an attached weight configured to position the straw in the liquid contained in the bottle when the bottle is inclined,
wherein the application of the portable terminal is configured to
   obtain recommended temperature information for formula preparation, the recommended temperature information based on formula information obtained through the portable terminal, and
   transmit the recommended temperature information from the portable terminal to the bottle, wherein the bottle configures the formula preparation temperature according to the recommended temperature information received from the portable terminal, and wherein the formula information is obtained from an image captured by a camera of the portable terminal, the captured image including at least one of a Universal Product Code (UPC), a European Article Number 13 (EAN-13), a barcode, and a Quick Response (QR) code.

15. The method of claim 14, wherein the straw is made of an elastic material, and wherein the attached weight is disposed at a distal end of the straw.

* * * * *